(12) United States Patent
Geist et al.

(10) Patent No.: US 8,317,801 B2
(45) Date of Patent: Nov. 27, 2012

(54) METHOD AND APPARATUS FOR FACILITATING NAVIGATION OF AN IMPLANT

(75) Inventors: Wyatt Drake Geist, Davie, FL (US); Christopher Walsh, Parkland, FL (US)

(73) Assignee: Magrod, LLC, Davie, FL (US)

( * ) Notice: Subject to any disclaimer, the term of this patent is extended or adjusted under 35 U.S.C. 154(b) by 0 days.

(21) Appl. No.: 13/313,528

(22) Filed: Dec. 7, 2011

(65) Prior Publication Data
US 2012/0179213 A1    Jul. 12, 2012

Related U.S. Application Data

(63) Continuation of application No. 12/728,818, filed on Mar. 22, 2010, now Pat. No. 8,092,461, which is a continuation-in-part of application No. 12/157,397, filed on Jun. 10, 2008, now Pat. No. 7,976,546, which is a continuation-in-part of application No. 11/462,592, filed on Aug. 4, 2006, now Pat. No. 8,092,458.

(51) Int. Cl.
- *A61B 17/58* (2006.01)
- *A61B 17/60* (2006.01)
- *A61B 17/70* (2006.01)
- *A61F 2/00* (2006.01)

(52) U.S. Cl. .................... 606/99; 606/86 A; 606/914

(58) Field of Classification Search ................ 606/86 A, 606/99, 246, 250, 265, 270, 279, 914
See application file for complete search history.

(56) References Cited

U.S. PATENT DOCUMENTS

| | | | |
|---|---|---|---|
| 5,049,151 | A | 9/1991 | Durham et al. |
| 5,127,913 | A | 7/1992 | Thomas, Jr. |
| 5,514,145 | A | 5/1996 | Durham et al. |
| 5,797,911 | A | 8/1998 | Sherman et al. |
| 5,851,183 | A | 12/1998 | Bucholz |
| 6,074,394 | A | 6/2000 | Krause |
| 6,086,596 | A | 7/2000 | Durham |
| 6,127,597 | A | 10/2000 | Beyar et al. |
| 6,162,228 | A | 12/2000 | Durham |
| 6,168,595 | B1 | 1/2001 | Durham et al. |
| 6,226,548 | B1 | 5/2001 | Foley et al. |
| 6,236,875 | B1 | 5/2001 | Bucholz et al. |
| 6,503,249 | B1 | 1/2003 | Krause |
| 7,011,660 | B2 | 3/2006 | Sherman et al. |
| 7,835,778 | B2 | 11/2010 | Foley et al. |
| 7,976,546 | B2 | 7/2011 | Geist et al. |
| 8,092,458 | B2 | 1/2012 | Geist et al. |
| 8,092,460 | B2 | 1/2012 | Geist et al. |

(Continued)

FOREIGN PATENT DOCUMENTS

| WO | WO 2009105104 | 8/2009 |
|---|---|---|

(Continued)

*Primary Examiner* — Kevin T Truong
*Assistant Examiner* — Sameh Boles
(74) *Attorney, Agent, or Firm* — McHale & Slavin, P.A.

(57) ABSTRACT

The present invention describes a targeting system suitable for guiding a biocompatible device to a target area within the body (in vivo) and method of using the same. The system includes a targeting member that is attached to the biocompatible device and may optionally include a steering material. The system includes a passer element located at the distal end of a wand. The wand includes a trigger like member adjacent a hand grip. Actuation of the trigger like member will result in a pivotal movement of the passer element that positions the targeting member such that the connected biocompatible device is positionable relative to the target area.

16 Claims, 17 Drawing Sheets

U.S. PATENT DOCUMENTS

| | | |
|---|---|---|
| 8,092,461 B2 | 1/2012 | Geist et al. |
| 2003/0065373 A1 | 4/2003 | Lovett et al. |
| 2005/0055089 A1 | 3/2005 | Macoviak et al. |
| 2005/0075562 A1 | 4/2005 | Szakelyhidi, Jr. et al. |
| 2005/0085714 A1 | 4/2005 | Foley et al. |
| 2005/0277934 A1 | 12/2005 | Vardiman |
| 2006/0079894 A1* | 4/2006 | Colleran et al. ............ 606/61 |
| 2006/0149135 A1 | 7/2006 | Paz |
| 2007/0191836 A1 | 8/2007 | Justis |
| 2007/0191845 A1 | 8/2007 | Justis et al. |
| 2007/0213714 A1 | 9/2007 | Justis |
| 2008/0039845 A1 | 2/2008 | Bonutti et al. |
| 2008/0140100 A1 | 6/2008 | Gertner |
| 2008/0312704 A1 | 12/2008 | Hestad et al. |
| 2009/0287255 A1 | 11/2009 | Erickson et al. |
| 2011/0238117 A1 | 9/2011 | Geist et al. |

FOREIGN PATENT DOCUMENTS

| | | |
|---|---|---|
| WO | WO 2009152243 | 12/2009 |

* cited by examiner

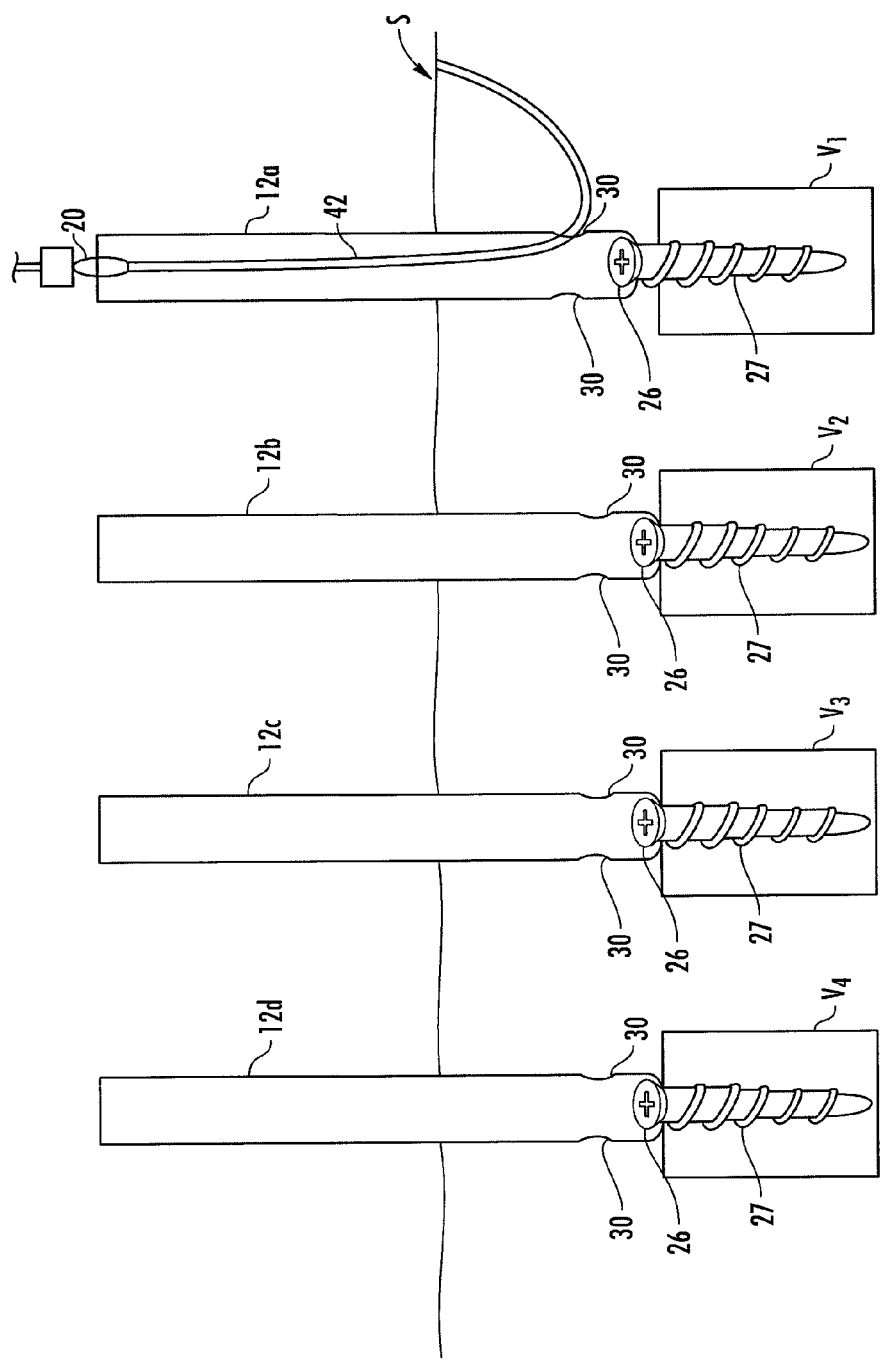

METHOD AND APPARATUS FOR FACILITATING NAVIGATION OF AN IMPLANT

CROSS REFERENCE TO RELATED APPLICATIONS

This application is a continuation of U.S. application Ser. No. 12/728,818, filed Mar. 22, 2010, now U.S. Pat. No. 8,092,461 entitled "Method and Apparatus for Facilitating Navigation of an Implant", which is a continuation-in-part of U.S. application Ser. No. 12/157,397, filed on Jun. 10, 2008, entitled, "Magnetic Targeting System For Facilitating Navigation", which is now issued U.S. Pat. No. 7,976,546 on Jun. 22, 2011, which is a continuation-in-part of U.S. application Ser. No. 11/462,592, filed on Aug. 4, 2006, now U.S. Pat. No. 8,092,458 entitled, "Magnetic Targeting System and Method of Using The Same," which are hereby expressly incorporated by reference.

FIELD OF THE INVENTION

The invention generally relates to surgical implants; particularly to a system and method for stabilization of adjacent bony structures; most particularly to a system to help navigate an interconnecting means between multiple bony stabilization devices.

BACKGROUND OF THE INVENTION

It is widely held that healing and/or structural correction is greatly facilitated when a bone is stabilized in the proper position. Various devices for stabilization of bone are well known and routinely practiced in the medical arts. For example, an abnormal spine can be stabilized using a substantially rigid or semi-rigid interconnecting means (rod or plate) and fastening means (screws, clamps, hooks, claws, anchors, or bolts). Multiple fasteners are placed into the spinal pedicle of each vertebra and linked by at least one interconnecting means. One of the more difficult aspects is the surgical insertion of the interconnecting means along a fixed path of delivery longitudinally along the vertebrae and through each of the multiple fastening means between multiple vertebrae. Once in place, this system substantially immobilizes the spine and promotes bony fusion (arthrodesis).

Traditionally, the surgical techniques for stabilization of bone required large incisions (upwards of 6 cm in length) and a considerable amount of muscle to be cut and stripped away (retracted) from the bone for an "open" visualization of the bone and access thereto for the placement of the fasteners and instrument implantation. Although this so-called "open" surgical technique has successfully treated non-unions, instability, injuries and disease of the spine, it is not without disadvantages. Given the invasive nature of this technique, a lengthy healing time and considerable post-operative pain for the patient is common.

In response to aforementioned drawbacks, the surgical arts have developed minimally invasive systems and procedures intended to replace the more traditional open surgeries. Obviously, a less extensive system and procedure will eliminate the need to perform much of the cutting and stripping of muscle, resulting in reduced recovery time and less post-operative pain. As a result, percutaneous procedures have been developed which insert instruments and perform operations through small skin incisions, usually between 1.5 and 5 cm in length, thereby reducing soft tissue damage. However, smaller skin incisions and smaller surgical fields require more novel and innovative approaches to perform these complicated surgeries.

One such example of a minimally invasive system is the SEXTANT Spinal System by Medtronic (Memphis, Tenn.). This device is comprised of two basic components, screw extenders and the rod inserter, which results in an instrument that looks like a sextant used in naval navigation. The device is an insertion tool that allows fasteners and interconnecting means to be applied to the spine in a minimally invasive manner. The screw extenders are long shafts used to deliver and attach screws to the vertebrae through small skin incisions. During surgery, these extenders protrude outside the body, allowing the surgeon to arrange and join their ends so that the rod inserter may be attached. The rod inserter is an arc-shaped arm that swings along a fixed axis and pushes an interconnecting rod though the skin and muscle and into the heads of the implanted fasteners (pedicle screws).

While the aforementioned technique is adequate when the fastening means are well aligned, it fails to deliver the rod when one of the screws is misaligned. Moreover, the interconnecting rod must be pushed by the surgeon along a fixed arch and cannot be directed around neural structures or bony obstructions. One consequence of forcibly pushing the rod through the fastening means is the possibility of collision between the rod and a bony obstruction, causing a piece of bone to break off, resulting in possible neurological damage. Another common problem is the interconnecting rod becoming disengaged from the rod inserter. When either of these incidents happens, additional surgery is often required to remove the bone fragment and rod from the wound. This may result in the surgeon abandoning the minimally invasive approach and reverting to a traditional approach. Current spinal implant systems do not allow the contour of the rod to match the normal curvature of the surrounding anatomy, and such systems are not customizable to meet the individual anatomical variables that each patient presents.

In order to help avoid damaging sensitive anatomy and expedite implant assembly, various image-based navigation systems have been employed which utilize patient images obtained prior to or during the medical procedure to guide a surgeon during the surgery. Recent advances in imaging technology have produced detailed two and three dimensional images using optically guided, fluoroscopic guided, and electromagnetic field based systems. These image-based systems have also been used in combination with the previously described "open" surgeries. One significant problem with most image-based systems is that the radiation generated is transmitted to the patient and surgical staff, which may result in physiological damage over time. Also, the cost and portability of this equipment continue to be an issue. In addition, these systems often require the surgeon to undergo extensive training to operate correctly.

Accordingly, a need exists in the surgical arts for a system and minimally invasive procedure capable of providing optimal mechanical support and bony fusion, while reducing the likelihood of bone damage and neural functioning when compared to the currently available interconnecting elements. It is also desirable to provide a surgical procedure that can be performed in conjunction with, but does not require, an image-based tracking system.

PRIOR ART

Although there are numerous patents directed to systems and methods for insertion of a stabilizing implant at a selected area of an anatomy, the prior art nevertheless fails to teach a targeting system for the insertion of an implant using minimally invasive techniques having a decreased risk of causing damage to neural structures or bony obstructions using minimal, if any, radiation exposure to the patient and/or surgeon.

For example, U.S. Publication No. 2005/0085714 to Foley et al., discloses a method and apparatus for percutaneous and/or minimally invasive implantation of a construct (e.g., spinal implant). The construct may be implanted using a navigation system for planning and execution of a procedure. A plurality of portions of the construct may be interconnected using locations and paths determined and navigated with the navigation system. The navigation system utilizes optical or electromagnetic localization to determine the precise location of a selected implant construct or instrument. An optical localizer can be positioned relative to an extender attached to a screw. Alternatively, a coil may be positioned in an electromagnetic (EM) field such that the position of the coil may be determined by sensing the induced voltage. A computer is used to form a plan prior to implantation of the construct and thereafter track the various portions of the construct during insertion. The plan and the tracking of the surgery are displayed on a monitor to provide guidance to the surgeon.

U.S. Publication No. 2005/0277934 to Vardiman, discloses a minimally invasive spinal fixation system used for spinal arthrodesis (bony fusion) or motion preservation. The system comprises a plurality of pedicle screws, including a first screw placed into a first vertebral body, and a second screw placed into a second vertebral body, a connector for attaching to the first and second screws, and a removable guide for percutaneously attaching the connector to the first and second screws. According to one embodiment, detectional spheres are positioned on the head of screw extenders and on the handle of the rod insertion tool. A comparator calculates the relative position of the insertion tool handle with respect to the screw extenders and provides a visual display for the surgeon.

U.S. Pat. No. 6,236,875 to Bucholz, discloses surgical navigation systems including reference and localization frames. The system generates an image representing the position of one or more body elements during the procedure using magnetic resonance imaging (hereinafter, MRI) or computed tomography (hereinafter, CT) scan images taken prior to the surgery. The body elements and their relative position are identified during the procedure. The position of the known body elements can then be manipulated using a computer to the relative position of the patient during the surgery. The manipulated data can then be utilized to guide the surgeon for implantation.

U.S. Pat. No. 6,226,548 to Foley et al., discloses an apparatus and procedures for percutaneous placement of surgical implants and instruments such as, for example, screws, rods, wires and plates into various body parts using image guided surgery. The invention includes an apparatus for use with a surgical navigation system, an attaching device rigidly connected to a body part, such as the spinous process of a vertebra, with an identification superstructure rigidly but removably connected to the attaching device. This identification superstructure, for example, is a reference arc and fiducial array which accomplishes the function of identifying the location of the superstructure, and, therefore, the body part to which it is fixed, during imaging by CT scan or MRI, and later during medical procedures. The system utilizes emitters such as light emitting diodes (hereinafter, LEDs), passive reflective spheres, acoustics, magnetics, electromagnetics, radiologic, or micro-pulsed radars for indicating the location of a body part to which the emitter is attached.

U.S. Pat. No. 7,011,660 to Sherman et al., discloses a brace installation instrument and method for the stabilization of bony structures. The installation instrument is a sextant-type tool with anchor extensions coupled to the anchors. The instrument is movable with respect to the anchors to position a brace in a position proximate to the anchors. The brace can be indexed for insertion at a predetermined orientation with respect to the installation instrument.

All of the aforementioned prior art disclose systems which utilize an implant insertion means to forcibly push the surgical implant or instruments to the target area in vivo. This increases the possibility of pathway divergence and/or damage to neural and vascular structures. What has been heretofore lacking in the prior art is a simple and economical system and procedure for the accurate and precise placement of surgical implants and/or instruments at a target area while providing a decreased risk to neural and vascular structures. Moreover, none of the aforementioned references provide audible and/or tactile feedback to the surgeon that indicates the target area has been reached.

SUMMARY OF THE INVENTION

The instant invention is related to a system suitable for guiding a biocompatible device, (implant, surgical instrument) to a target area within the body (in vivo), be it a tumor or implantation point for a fastening means. The system includes a passer element located at the distal end of a wand. The wand includes a trigger like member adjacent a hand grip. Actuation of the trigger like member will result in a pivotal movement of the passer element that positions the targeting member such that the connected biocompatible device is positionable relative to the target area.

It is therefore an objective of the instant invention to provide a system that minimizes soft tissue damage and provides less post-operative pain.

Yet another objective of the present invention is to provide a device and/or system that permit percutaneous positioning of a biocompatible device via a tether which may be utilized to pull the implant into position.

Another objective of the present invention is to provide a device that can percutaneously pass a tether along the vertebrae to treat scoliosis patients.

Still a further objective of the invention is to teach a device and/or system which allows for shorter surgery, decreased x-ray exposure, and fewer complications for the patient.

Yet another objective of the instant invention is to provide a device and/or system that is simple to operate to reduce the training the surgeon must undergo for operation of peripheral systems.

These and other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments illustrate various objects and features thereof.

BRIEF DESCRIPTION OF THE FIGURES

FIGS. 11A, 11B, 11C, 11D, 11E and 11F illustrate various steps necessary to position the targeting member such that the connected biocompatible device is positionable relative to multiple target areas.

DETAILED DESCRIPTION OF THE INVENTION

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

Figure 1:
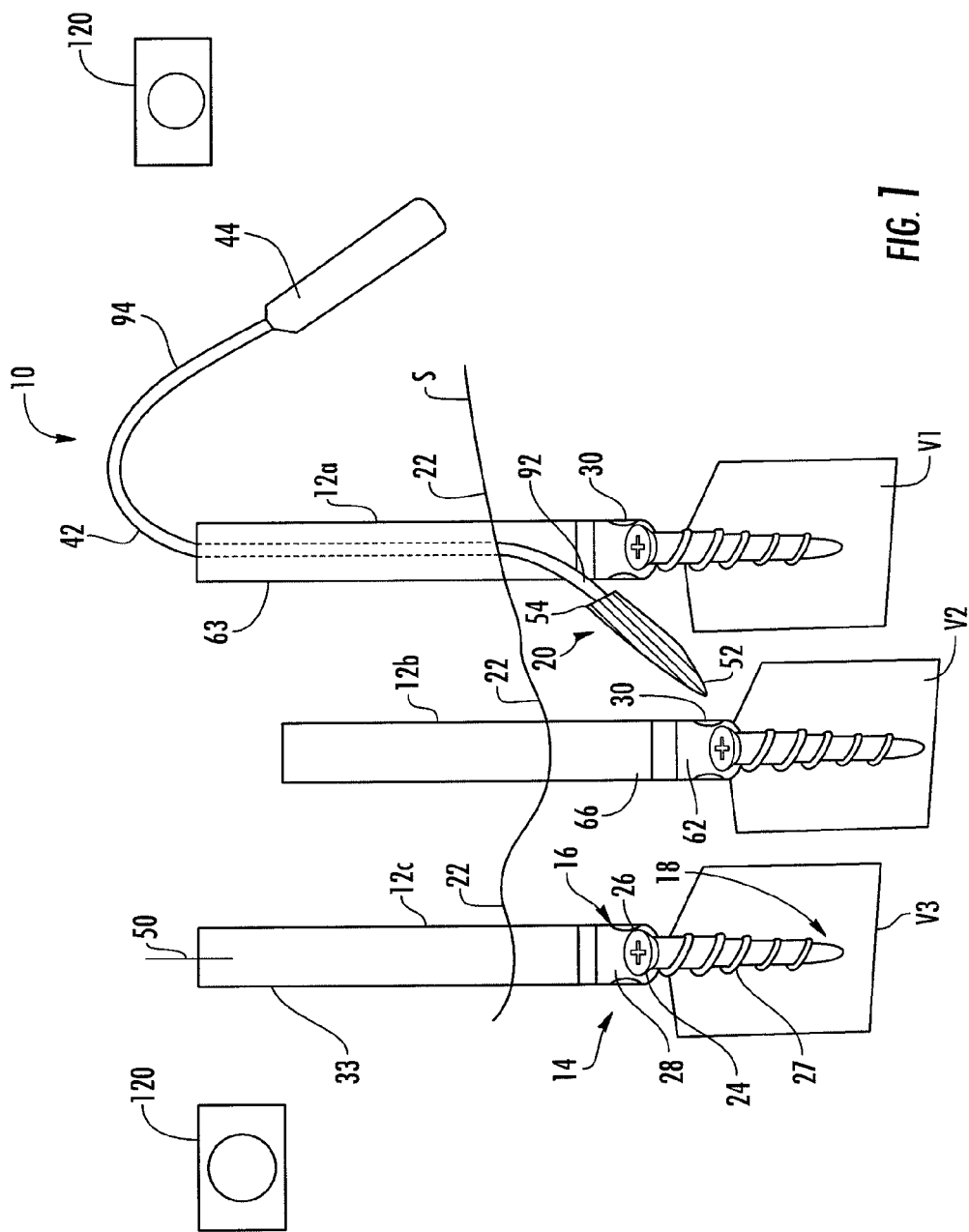
FIG. 1 illustrates a partial side view of a portion of a patient's spine which includes a targeting system according to a preferred embodiment of the invention.
Figure 2:
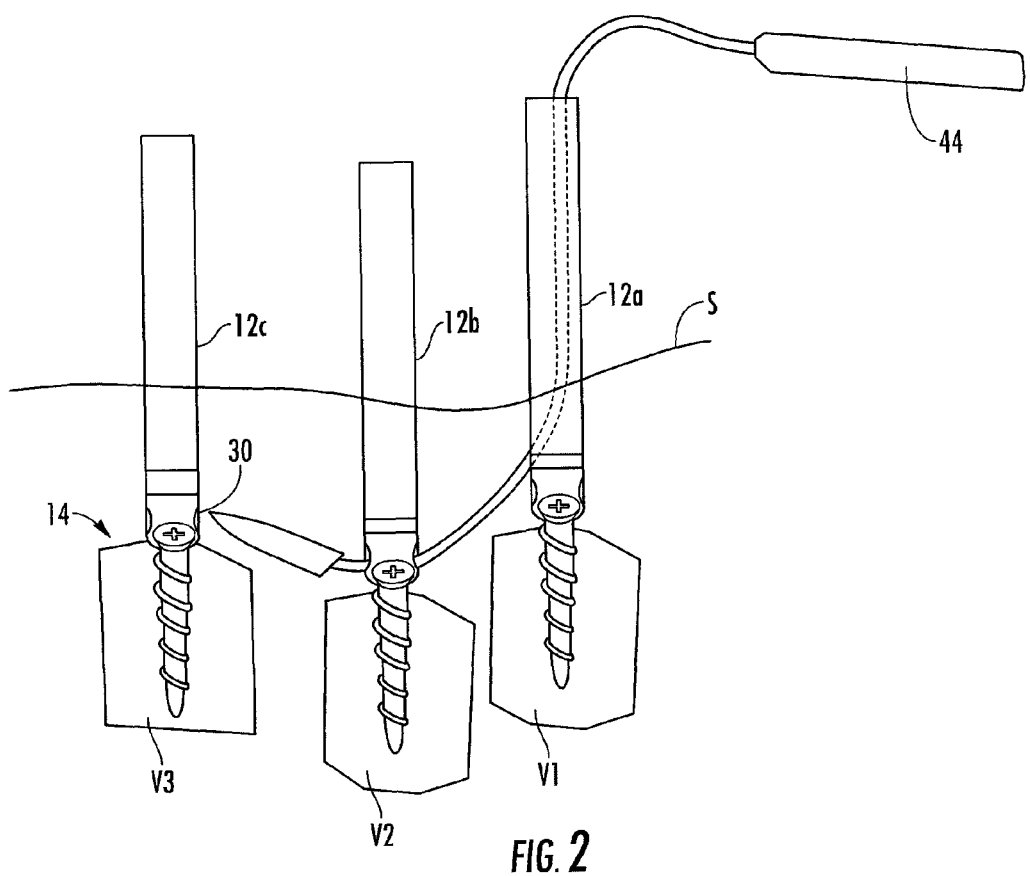
FIG. 2 is the targeting system as shown in FIG. 1, illustrating the targeting member with attached tethering means threaded through an anchor member.
Figure 3:
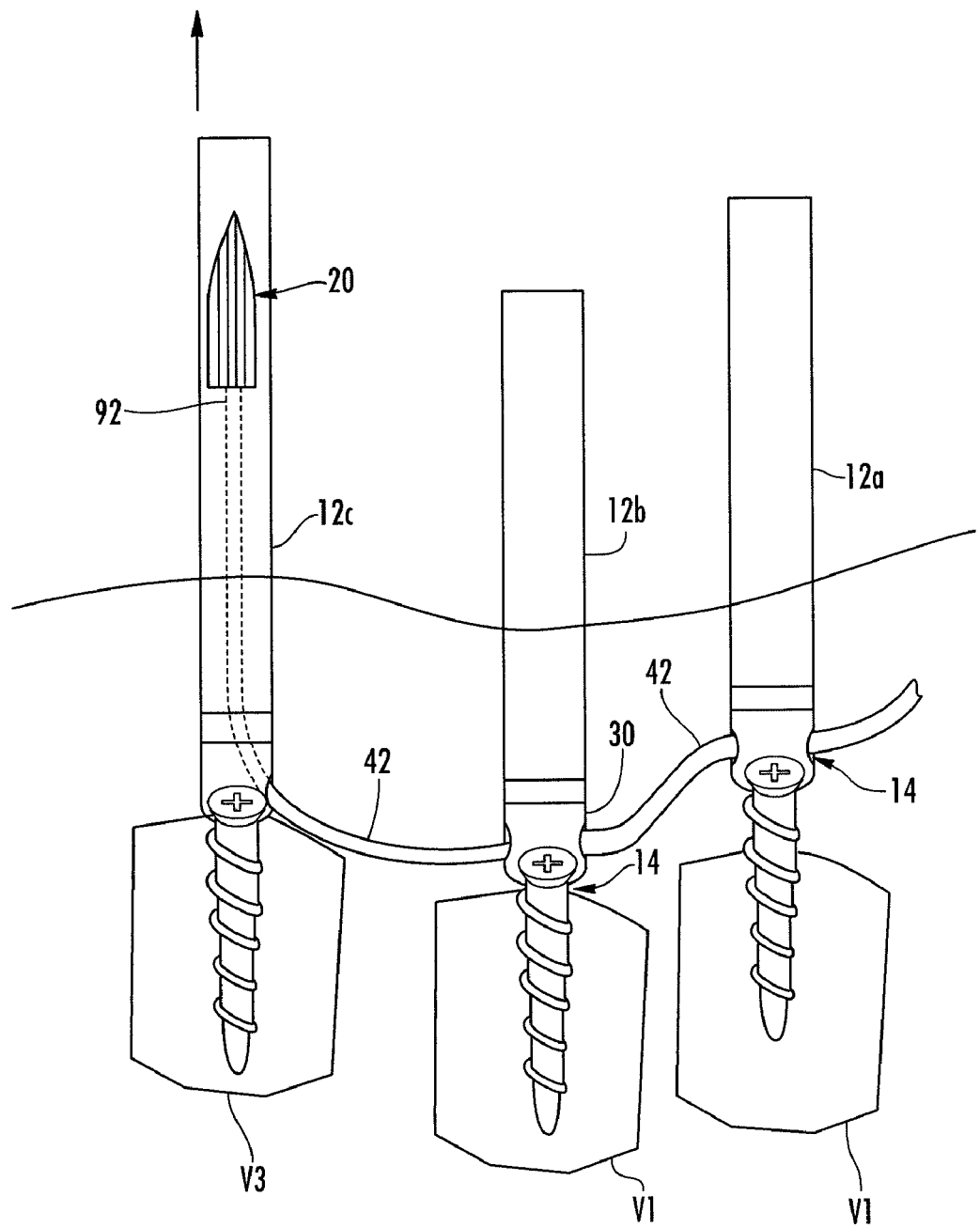
FIG. 3 is the targeting system shown in FIG. 1, illustrating the targeting member being removed from the interior of the patient through the last extender.

Referring now to FIGS. 1-8 which illustrate the targeting system 10 of the present invention suitable for facilitating navigation to a target area, wherein like elements are numbered consistently throughout. FIG. 1 shows a plurality of anchoring members 14 (also referred to as fastening means). The anchoring members are depicted here as multi-axial pedicle screws, each removably attached to an extender 12a, 12b, and 12c. These screws have a proximal end 16 and a distal end 18. The proximal end includes head portion 24 with a tool opening 26 configured to receive a driving tool (not shown). The distal end 18 includes a threaded shank 27 designed to secure to a selected target area located inside the body of a patient (in vivo), shown here as consecutive spinal vertebrae V1, V2, V3. Although the target area is exemplified here as vertebrae in a partial spinal column, the target area may be located anywhere in vivo.

The screw shown here is a multi-axial screw where the proximal end of the screw may include a connector 28 rotatably connected to the head portion 24 of the screw. That is, the connector is capable of 360 degree rotation relative to the threaded shank 27 of the screw along the axis L (FIG. 5) of the shank. One example of a suitable multi-axial screw is described in U.S. Pat. No. 5,797,911, herein incorporated by reference. Although a multi-axis is exemplified herein, it is contemplated that a fixed axis screw may be used. Fixed-axis screws do not include a rotatable connector 28. Other means for anchoring are also contemplated herein, some of which include, clamps, hooks, claws, bolts, or the like. Moreover, the shank of the anchor member may or may be not be cannulated, as is known in the art.

Figure 4:
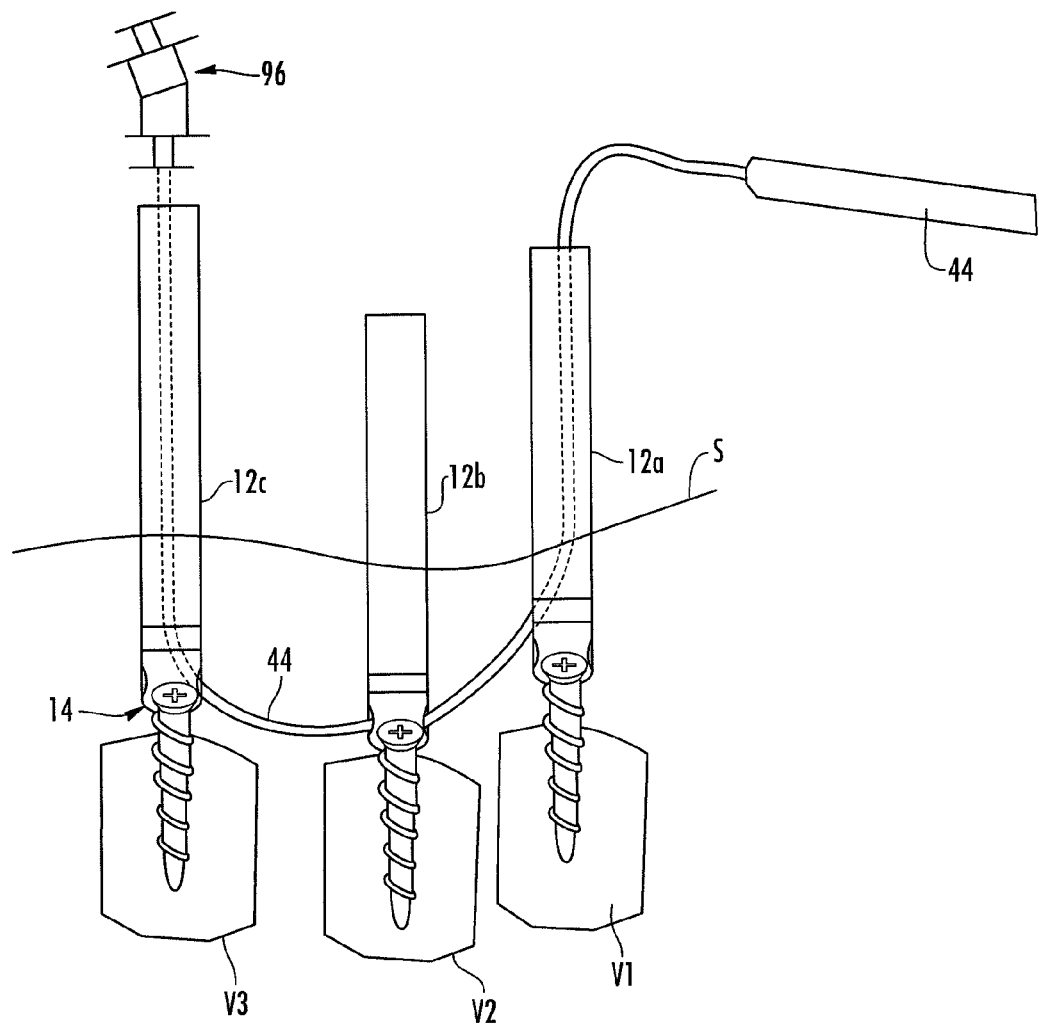
FIG. 4 is the targeting system as shown in FIG. 1, illustrating the insertion of the biocompatible device between adjacent vertebrae.
Figures 5, 6:
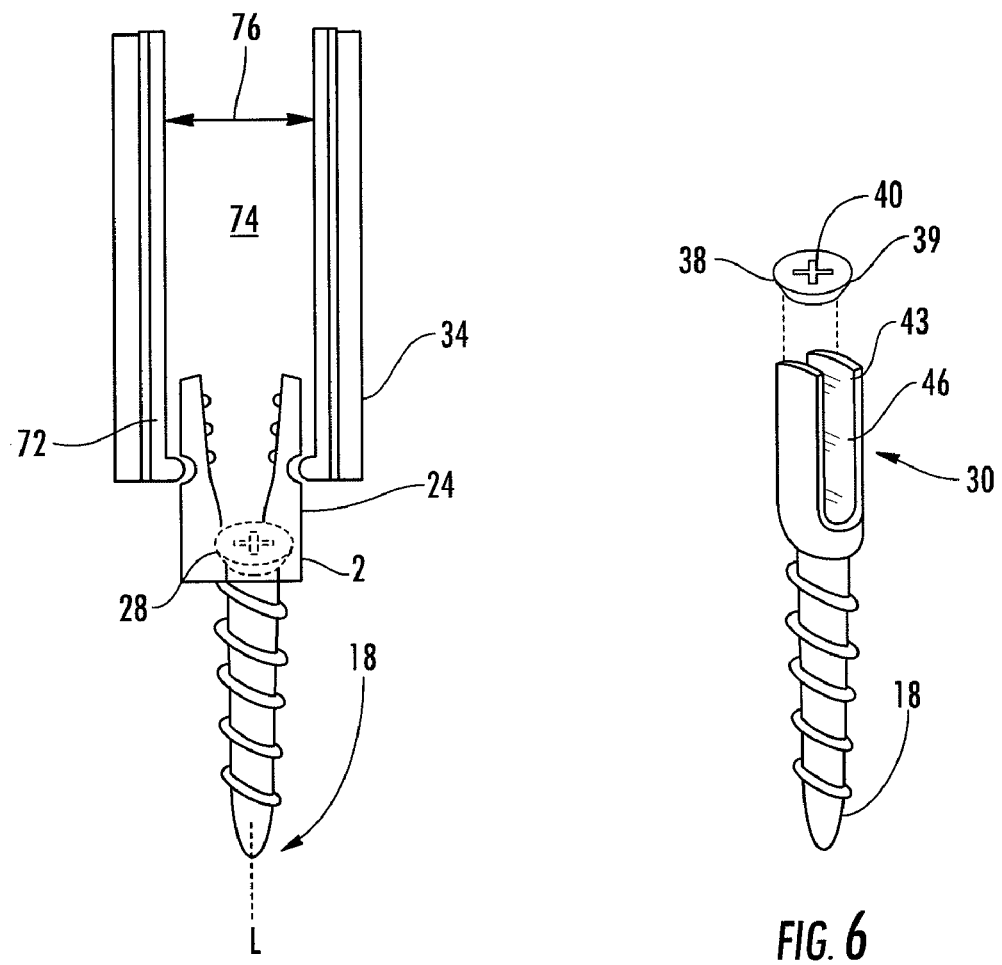
FIG. 5 is a partial cross-sectional view of a portion of the extender removably attached to the connector portion of the multi-axial screw in accordance with one embodiment.
FIG. 6 is an upper perspective view of a multi-axial screw that can be used in the system of the present invention.

As shown in FIGS. 5 and 6, the connector portion of the screw is constructed and arranged to form a passageway 30 designed to removably receive implants of various sizes. The connector portion includes an opening 43 constructed and arranged to receive a set screw 38. As shown in FIG. 6, the head portion 24 includes threaded interior sidewalls 46 designed to mate with external threads 39 formed on the set screw 38. Thus, as the set screw is threadably lowered along the connector portion of the screw, the passageway 30 in the connector is narrowed. The passageway is narrowed until the exterior surfaces of the biocompatible device 44 (shown here as an interconnecting rod, see FIGS. 1-4) are sandwiched between the upper portion of the screw head 24 and the set screw. This acts to reliably secure the biocompatible device onto the screw. As with the head of the screw, there should be a tool opening 40 configured to receive a driving tool (not shown) inserted within the interior portion 74 of the extenders. The driving tool is well known in the surgical arts, and is used to rotatably secure the set screw to the desired position within the interior of the connector.

As discussed above, the distal end 34 of each of the hollow extenders 12a, 12b, 12c are removably attached to the screws by any appropriate means known in the art. For example, the extender may include a depressible member (not shown) located at the proximal end 33 of the extender that is operatively connected to an internal clamping member located at the distal end thereof. The clamping member is capable of engaging and disengaging the connector portion of the screw. One example of a suitable extender which could be used in the present invention is disclosed in U.S. Pat. No. 7,011,660, herein incorporated by reference. The extender may also be able to rotate the connector of a multi-axial screw relative to the shank to facilitate the threading of the interconnecting rod therethrough.

The extenders should be made of a substantially rigid biocompatible material and have a length dimension (along its longitudinal axis 50) that allows the proximal end 33 to protrude a distance outside of the percutaneous exposure 22 created through the outer skin S of the patient. According to a preferred embodiment, at least the first extender should have a "c-shape", as seen along an axis transverse its longitudinal axis, thereby defining a slot 63 that extends along its longitudinal axis 50 and into the patient when attached to the screw. The slot should be sized to allow the targeting member to exit, so that it is able to be delivered percutaneously, as shown in FIG. 1. The interior dimension 76 of the extenders should be such that they are capable of receiving the appropriate driving tool (not shown) used to engage the screws and set screws. In addition, the interior dimension of the extenders should be able to accept a wand for passing the targeting member and a tool, such as a magnet or gripping device for removing the targeting member to a location outside of the extender and body, as described further below.

Referring again to FIGS. 1-4, a targeting member 20 is shown attached to a biocompatible device 44 by a tethering means 42. The biocompatible device 44 in turn is mounted on the leading end of a free hand inserter and is releasably secured thereto. The targeting member 20 has a first end 52 and a second end 54. The first end is designed to penetrate the tissue and is shaped to enlarge the opening while creating a pathway through the tissues as the targeting member 20 is advanced in vivo. At least the first end of the targeting member 52 is composed of a steering material capable of being magnetically influenced, as described hereafter. Alternatively, the targeting member 20 can be made from any non-magnetically influenced biocompatible material.

Figure 7A:
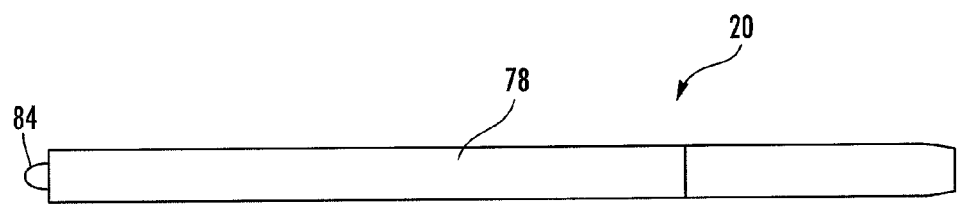
FIGS. 7A thru 7E illustrate various embodiments of the targeting member used in the instant invention.
Figure 7B:
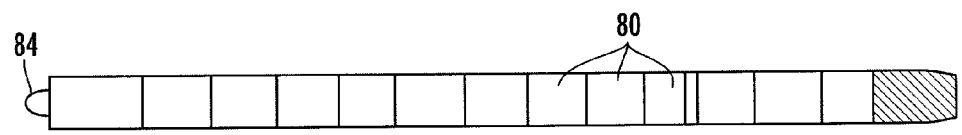
Figure 7C:
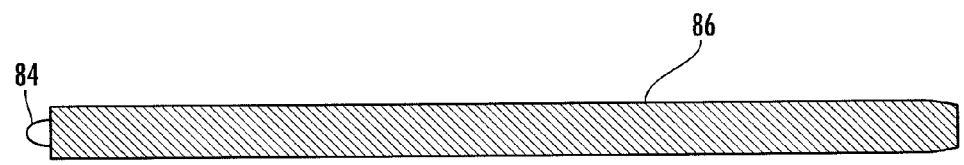
Figure 7D:
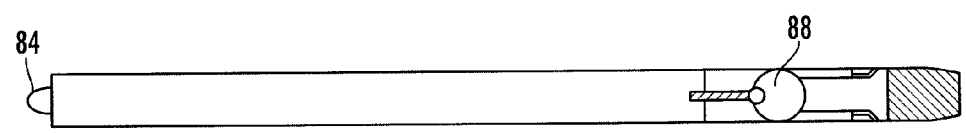
Figure 7E:
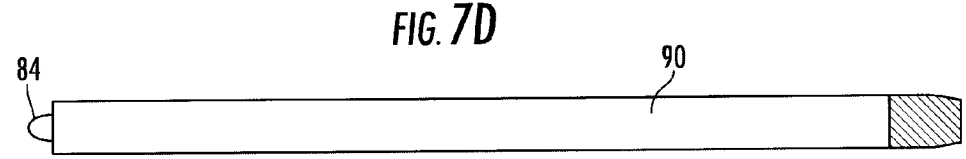

As shown in non-limiting embodiments of FIGS. 7A-E, the targeting member 20, which may be made from a flexible, semi-rigid, or rigid material, includes the steering material 84 located on the first end. FIG. 7A illustrates an embodiment of a semi-rigid targeting member in the form of a rod-like member with steering material 84 disposed on its first end 52. The first portion 78 of the rod is made of a flexible material capable of safely colliding with bony or neural obstructions without causing damage. FIG. 7B illustrates another flexible rod formed of a plurality of rigid consecutive segments 80 through which the tethering means 42 extends to the first end (not shown). When the surgeon pulls the tethering member at the second end taunt, the segments are forced together and little movement is permitted between the segments. In the embodiment of FIG. 7C, the entire targeting member is composed of or coated with a second biocompatible steering material 86. FIG. 7D illustrates another embodiment wherein the targeting member includes a ball joint 88 attached to the tethering means. As with the embodiment of FIG. 7B, the tension in the tethering member controls the amount of pivot at the ball joint. Thus, when tension is released, the rod becomes flexible and the first end of the targeting member pivots on the ball. Alternatively, when the tension is reapplied to the tethering means, the rod is solid again. This way the surgeon is able to safely guide the targeting member around neural and bony obstructions as it moves through the body. Lastly, FIG. 7E depicts a rigid rod-like member formed from solid biocompatible material 90.

The tethering means 42 may be made of any flexible or semi-flexible biocompatible material capable of allowing the device to navigate around neural and bony obstructions without damaging them. Examples of suitable tethering means may be in the form of a cable, cord or ligament. Moreover, the tethering means may be formed of a cannulated or solid member. As discussed above, the first end 92 of the tethering means is attached to the second end 54 of the targeting member by any means of attachment known in the art. Similarly, the second end 94 of the tethering means is attached to the biocompatible device 44 by any means of removable connection known in the art. For example, the biocompatible device and tethering means could include corresponding threads that the surgeon can rotate to disconnect the tethering means from the biocompatible device.

According to a preferred embodiment, the biocompatible device 44 is shown as an implantable interconnecting rod. The rod may be rigid, semi-rigid or flexible. Rigid rods are usually preferred for providing the necessary stability during the healing process and arthrodesis; however, flexible rods have been found to provide for arthrodesis while allowing some movement between bony structures that have been interconnected to preserve some motion. Moreover, like the tethering means, the biocompatible device 44 may also be solid or cannulated.

Although the interconnecting rod is shown in FIGS. 1-4 as interconnecting three pedicle screws, the surgeon could use any appropriately sized rod having a length dimension capable of interconnecting three or more fastening means co-linearly implanted along multiple vertebrae. It is also within the purview of the invention that any sized rod having various widths or diameters could be used so long as it is capable of stabilizing the bony structures for bony fusion. Although a rod-like member is exemplified herein, other such biocompatible devices known to one skilled in the art are also contemplated, for example, plates, clamps, etc.

FIG. 4 illustrates a hollow or cannulated flexible biocompatible device 44 in fluid communication with a cannulated tethering means. According to this embodiment, once the rod has been properly inserted into the desired location, the surgeon can use an insertion means 96 (syringe or the like) to supply a biocompatible hardening material (e.g., cement, carbon, bone matrix) through the tethering means and into the interior of the hollow rod. Although not required, the biocompatible device might also be made permeable and used to deliver constituents supplied by the insertion means to the target area (e.g., bone growth/fusion material, medication, curing material, etc.).

As shown in FIGS. 1-4, each of the proximal ends of the extenders 12a-c protrude outside of the patient's skin through percutaneous incisions 22 so that the surgeon is able to insert instrumentation through the extender's interior portion to access the screw secured to the target area (vertebra). The extenders also enable the surgeon to insert the wand or removal tool into the selected extender to a position proximate the corresponding anchor 14.

The "steering" material 84 in the targeting member 20, as used herein, refers to any material capable of being influenced by the magnetic material. For example, the steering material may include any magnetically attractive material or alloy, (e.g. steel, iron, etc). Moreover, the steering material may be coated with any suitable biocompatible element, such as plastic. The type, shape, and size of the magnetic material and steering material should be suitable for internal use in patients and provide the optimal magnetic field. Magnetic fields are used herein for navigating in vivo since these fields can penetrate human tissue and bone without being distorted similar to x-rays, but without the danger of radiation and physiologic damage.

Once the final vertebra is reached, the removal tool is used to pull the targeting member through the slot in the upper opening 43 of the pedicle screw and along the interior length of the extender until it reaches the proximal end protruding out of the incision. The surgeon can then grasp the targeting member and attached tethering means, see FIG. 3. The tethering means located outside the patient is then used by the surgeon to gently pull the attached biocompatible member (rod) along the path formed through the tissue by the targeting member and through the connector portion of the pedicle(s) until the biocompatible member reaches the last vertebra, as shown in FIG. 4.

If the tethering means and interconnecting rod are hollow, the user can disconnect the targeting member and releasably attach an injection means 96 thereto. The injecting means can be used to supply any suitable and flowable, biocompatible material inside the rod. One example of a suitable biocompatible material includes at least one hardening material that will cause the rod to become rigid.

Otherwise, the rod might be filled prior to the introduction of a hardening material. For example, the rod might contain ferroelectric material that allows the rod to remain flexible during the insertion process until exposed to an electric current. This is particularly suitable if used in conjunction with the electromagnet embodiment previously described. Once the flexible rod is positioned at the final desired location (secured to pedicle screws), the rod may then be exposed to electric current in the electromagnet by inserting the magnetic means into the extenders. The electric current causes the ferroelectric material to harden to make a substantially rigid rod. Thus, the contour of the rod corresponds to the natural curvature of the surrounding anatomy.

As discussed above, the connector portion of the screw is constructed and arranged to receive a set screw 38 therein. The set screw is inserted into each of the extenders and threadably attached by the driving tool (not shown). The biocompatible device 44, shown here as an interconnecting rod, is sandwiched between the upper portion of the head and the set screw. This acts to secure the rod onto the screws. The extenders are then removed from the connector portion of the screw and the exposures closed.

Figure 8:
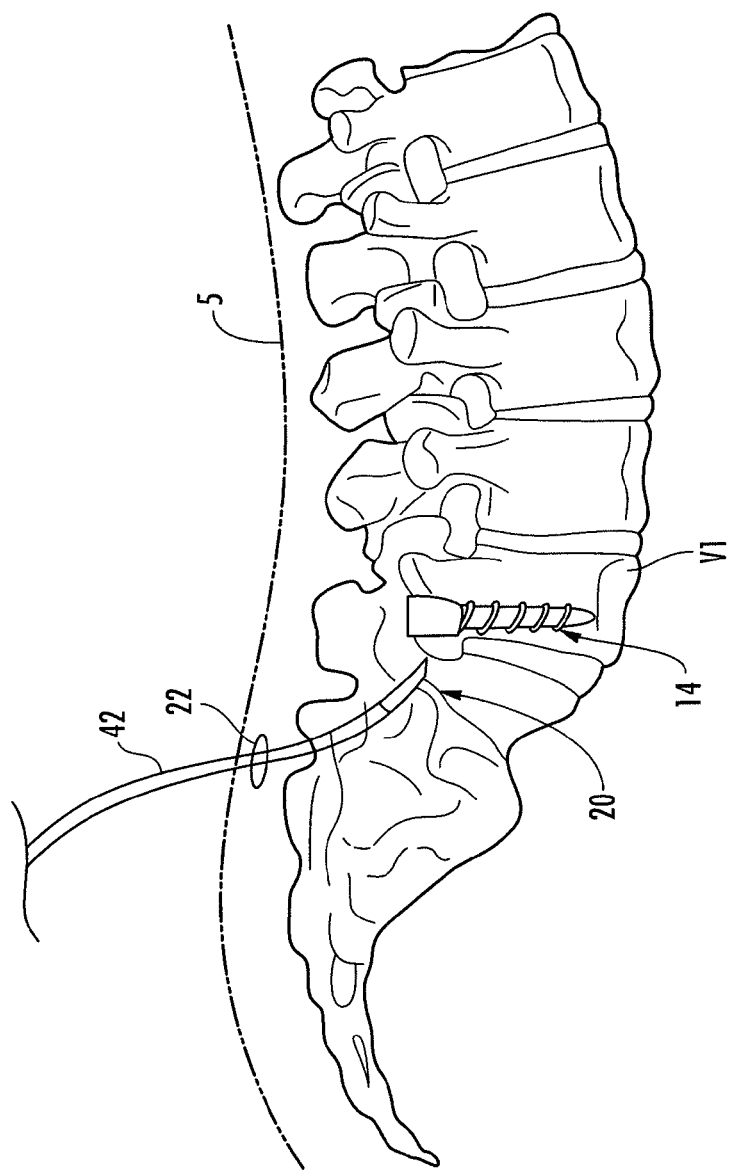
FIG. 8 is a partial side view of a portion of the spine of a patient which includes the magnetic targeting system according to another embodiment illustrating the insertion of the targeting member in vivo without the use of extenders.

Referring to an alternative embodiment shown in FIG. 8, the targeting system 10 of the present invention does not require the use of an extension member for insertion of the targeting member in vivo. The anchoring member may be implanted and the exposure closed with no external access thereto. The proximal end of the implanted anchoring member may include either a permanent magnet or a remotely controlled electromagnet, as is known in the art. Thus, the targeting member 20 may be directly inserted and fed into the body through incisions created by the surgeon. As with the previous embodiments, the magnetic portion of the anchoring member is capable of attracting or repelling the targeting member placed inside the patient. The targeting member 20 is passed from one incision to the next utilizing the wand and removal tool as will be described below.

Any of the aforementioned embodiments of the system and techniques of the present invention can employ any type of known imaging system to determine and locate placement of any of the aforementioned structures in vivo. For example, insertion of the anchor member into the bony structure can be pre-planned by CT scan, x-ray, or the imaging means known in the art.

The present system may also include a feedback system having at least one detection element 120 (two are shown in FIG. 1) disposed outside and proximate the patient to determine the position of the targeting member and/or biocompatible member in real-time. According to one, albeit non-limiting embodiment, the detection element is an audio receiver or pickup capable of audibly detecting when the targeting member and magnetic means connect or "click" together. This way, the surgeon can imagelessly determine that the targeting member has reached the magnetized portion of the anchoring member or removal tool. This may be used in conjunction with a tactile sensation produced when the targeting member and magnetic means connect. This tactile sensation of the two elements meeting will be felt by the person holding the tethering means.

Figure 9A:
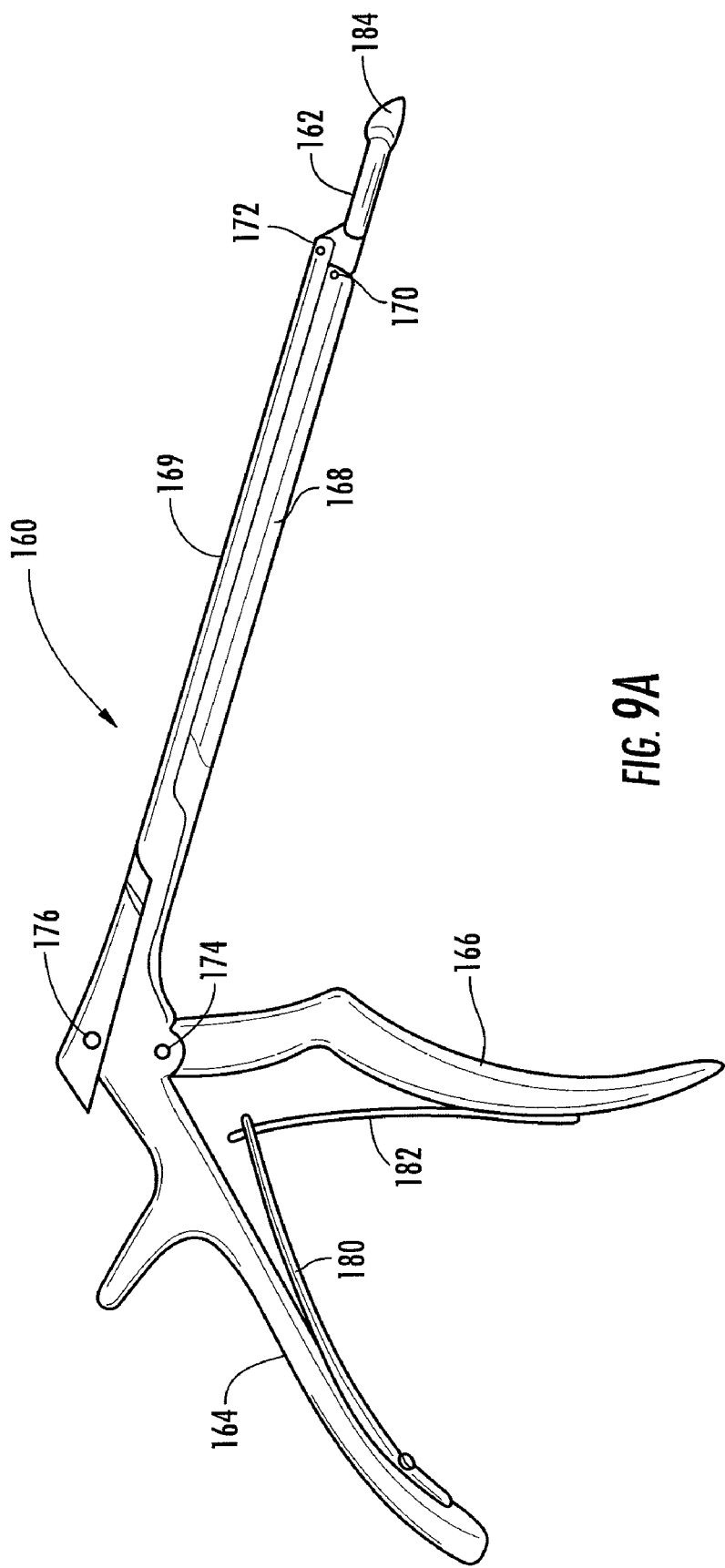
FIGS. 9A and 9B are perspective views of the wand that includes the passer element for the targeting member.
Figure 9B:
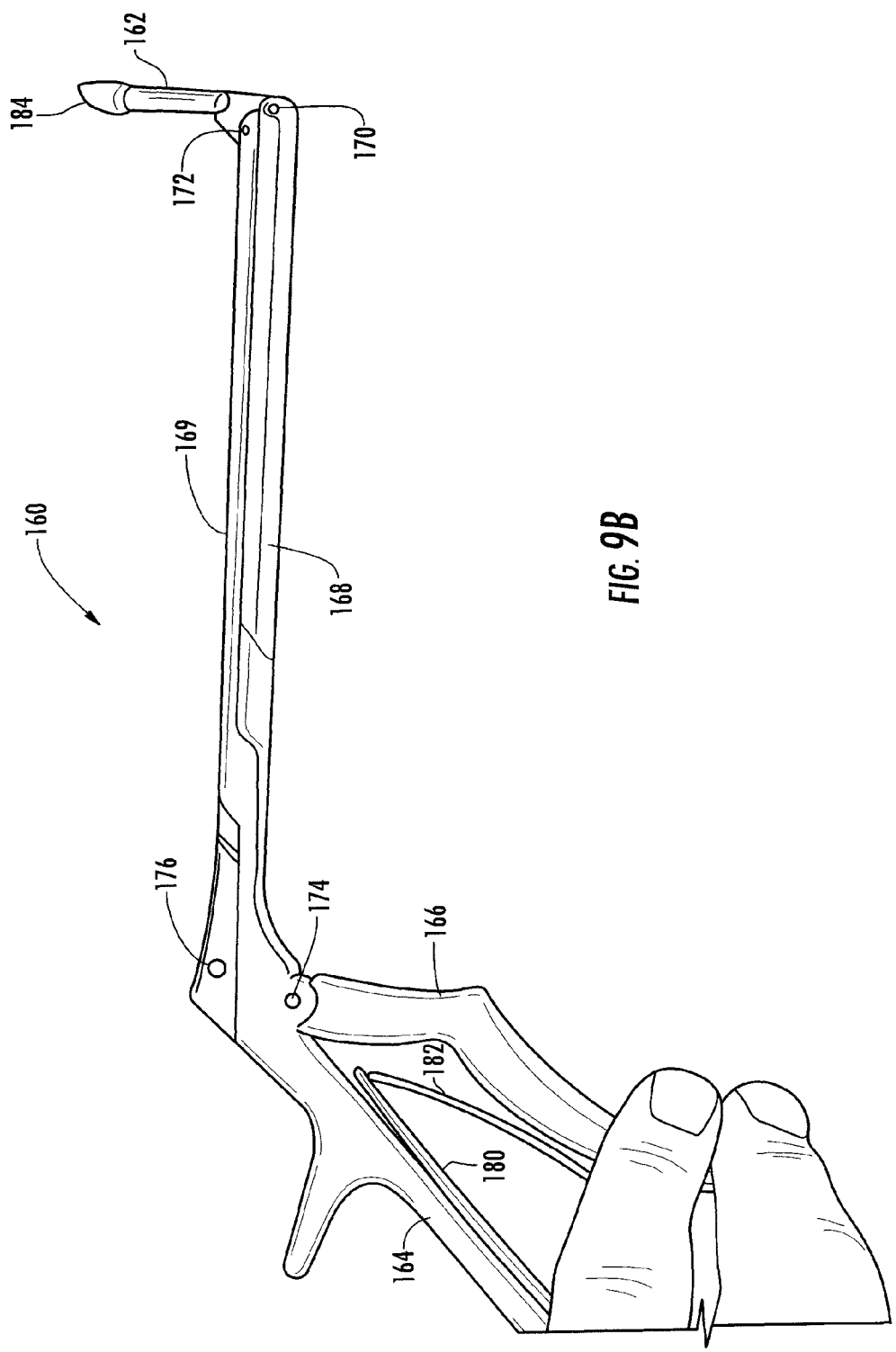

FIGS. 9A and 9B show the wand 160 with a pivotal passer member 162 located at the distal end of the wand 160. The wand 160 includes a hand holding grip 164 and a trigger like component 166 pivotally attached thereto. Hand grip member 164 includes an elongated rod like member 168. An additional rod like member 169 is positioned adjacent elongated rod member 168 and is hingedly connected to trigger 166, via pivots 176 and 174 at one end, and hingedly connected to passer member 162, via pivot 172 at the opposite end. Passer member 162 is also pivotally connected to elongated rod member 168 at pivot 170. Cantilevered flat springs 180 and 182 are positioned to bias the hand grip 164 and trigger 166 away from one another absent a force exerted by the operator's hand. In operation, the operator's fingers will grip trigger member 166 and pivotally move in towards the hand grip 164. When springs 180 and 182 abut the trigger and the hand grip they will act against the force exerted by the operator's fingers. The pivotal motion of trigger 166 relative to hand grip 164 will result in the relative axial displacement of rod like member 168 with respect to additional rod like member 169. The relative displacement will result in the pivotal movement of passer member 162, as shown in FIG. 9B, via the displacement of pivot 170 with respect to pivot 172. The wand 160, including passer member 162, is sized to fit within the internal cavity of extender 12. The passer member 162 includes a cavity 184 formed at its distal end that is sized and configured to receive the targeting member 20.

Figure 10A:
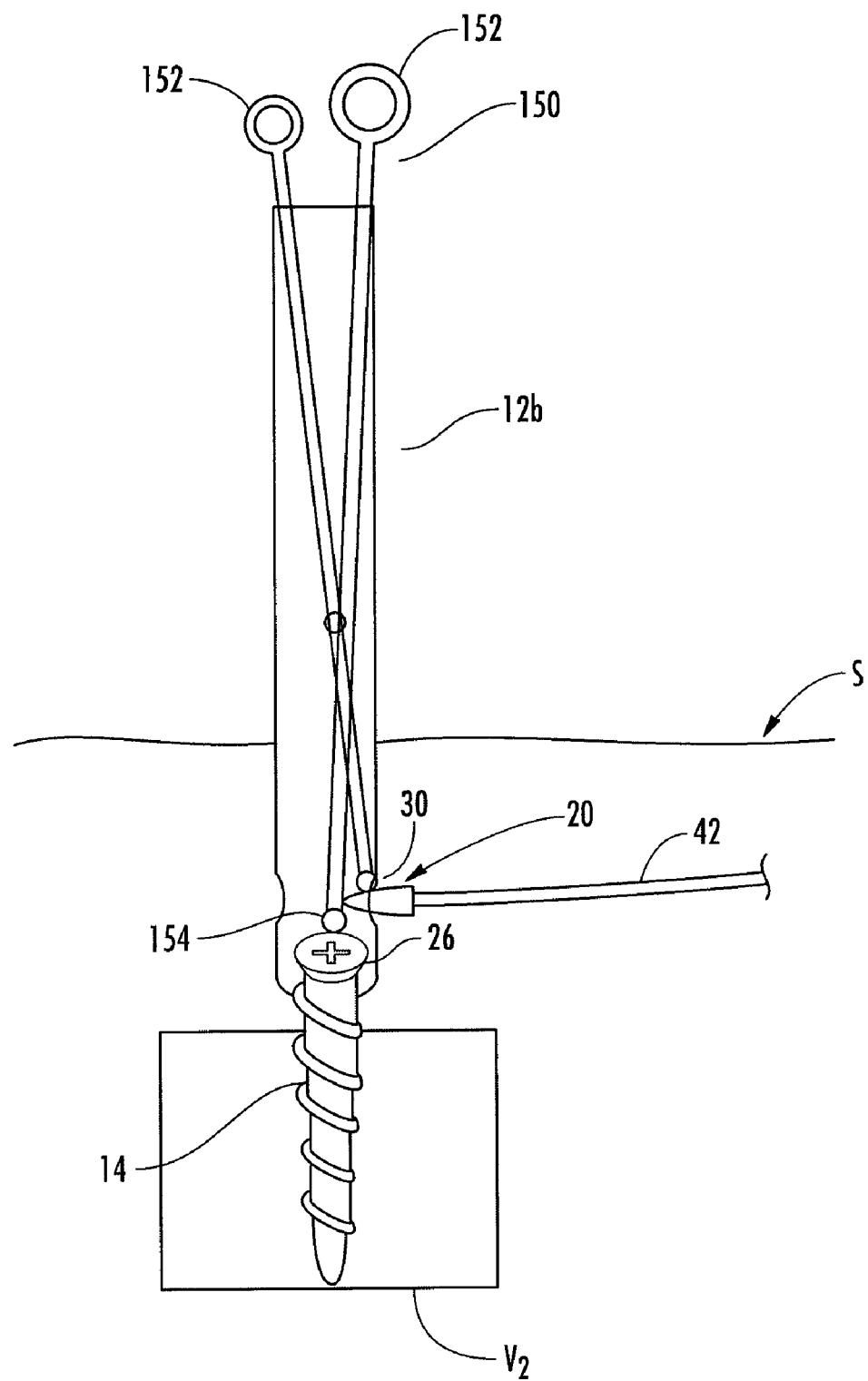
FIGS. 10A and 10B show alternative constructions for the targeting member removal tool.

FIG. 10A illustrates a first embodiment for a targeting member removal tool 150. Tool 150 is a mechanical gripping device that includes a pair of arms that are pivotally connected to one another at a position intermediate their respective ends. The upper end 152 of tool 150 is configured to be easily manipulated by the user's fingers and the lower end 154 is formed with surfaces designed to easily conform to the shape of targeting member 20. As shown, the targeting member 20 that is attached to tether 42 has been positioned adjacent the anchoring member 14 that has been threaded into vertebral body V2. The targeting member removal tool 150 is sufficiently small enough to easily extend into the bottom of the extender (shown here as 12B) and physically grab the targeting member 20. The tool 150 and targeting member 20 are thereafter withdrawn from the top or distal end of extender 12B.

Figure 10B:
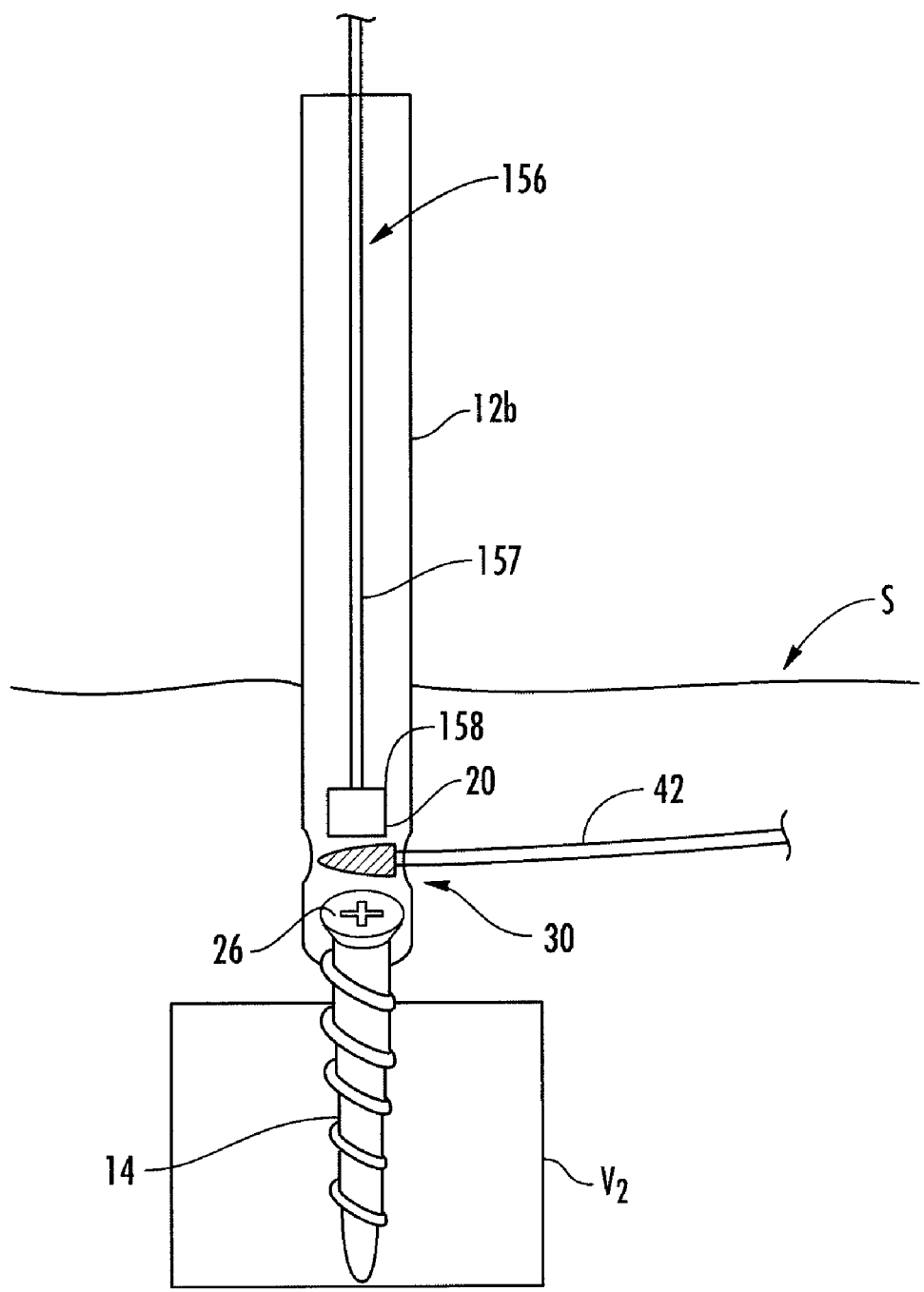

FIG. 10B shows an alternate embodiment for the targeting member removal tool 150 shown above. This embodiment is directed to a magnetic targeting member removal tool 156. Removal tool 156 includes an elongated shaft 157 having a permanent magnet 158 attached at a distal end. The proximal end of shaft 157 is manipulated such that the magnet will attract the targeting member 20. In this embodiment, the targeting member is at least partially made from a magnetically steerable material such as a permanent magnet or ferrous material. In this instance, the targeting member 20 and the magnet on the magnetic removal tool 156 are drawn towards one another and upon contact remain firmly attached. Once firmly attached, the removal tool 156 is withdrawn from the extender (shown here as 12B).

Figure 11A:
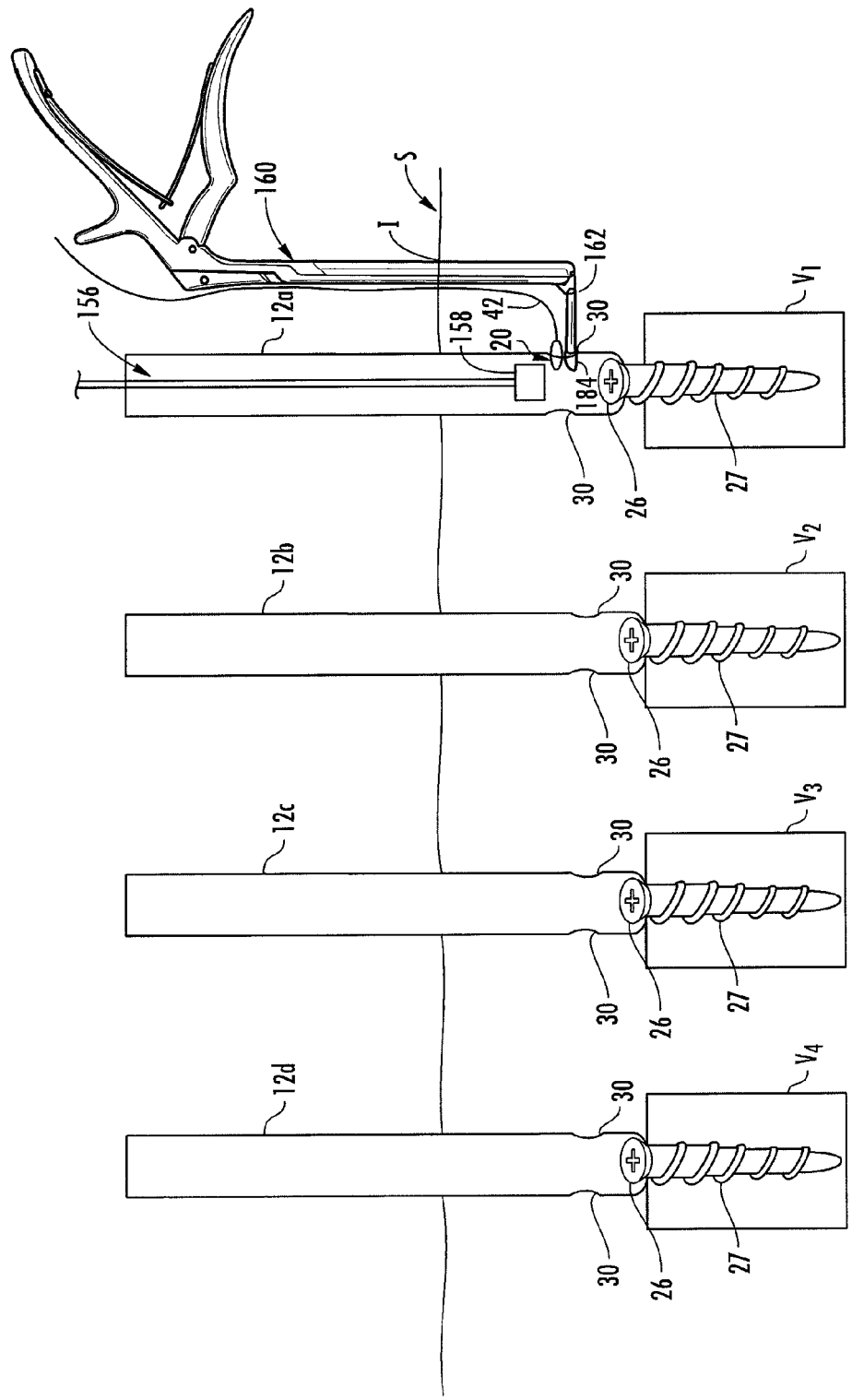
Figure 11C:
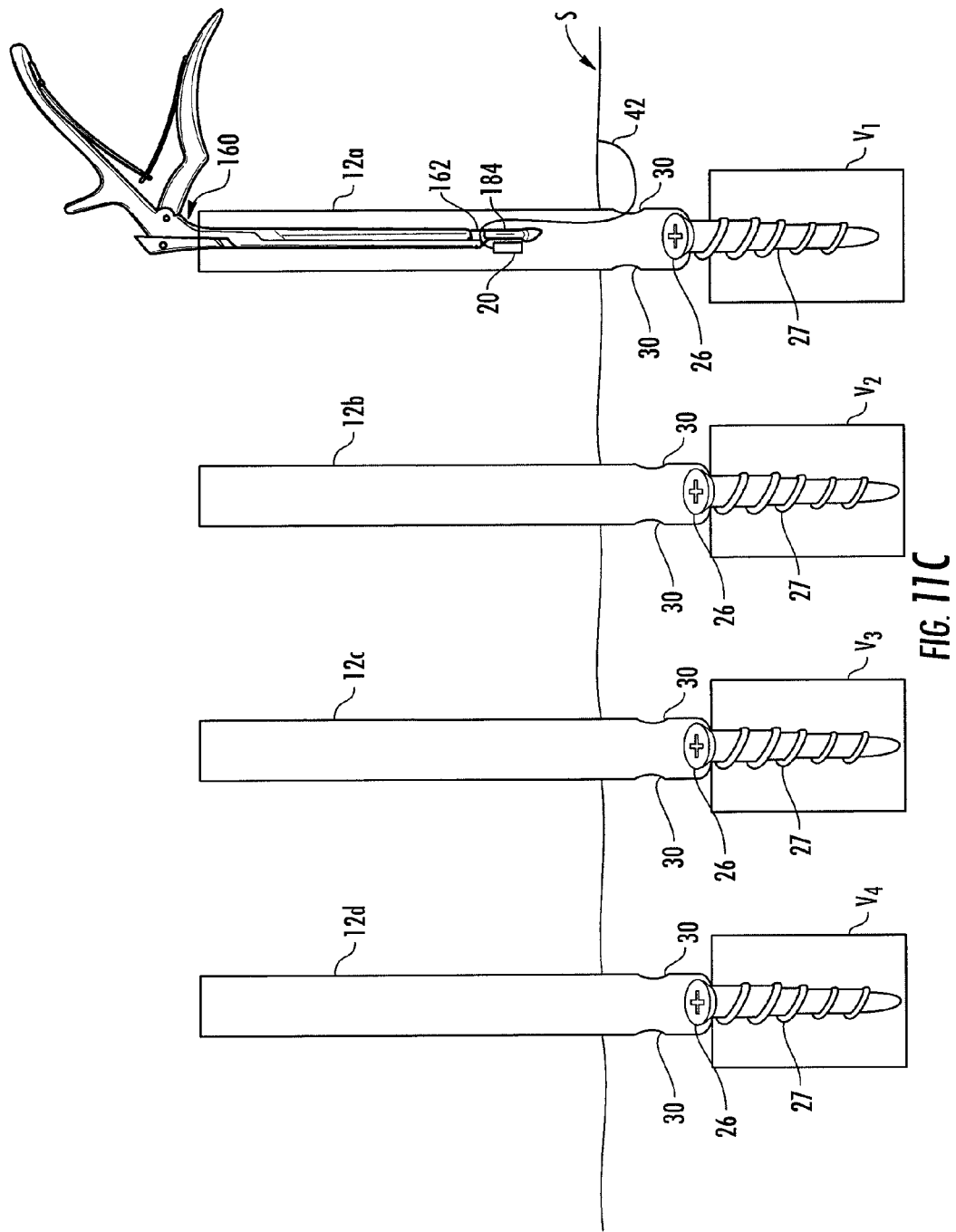
Figure 11D:
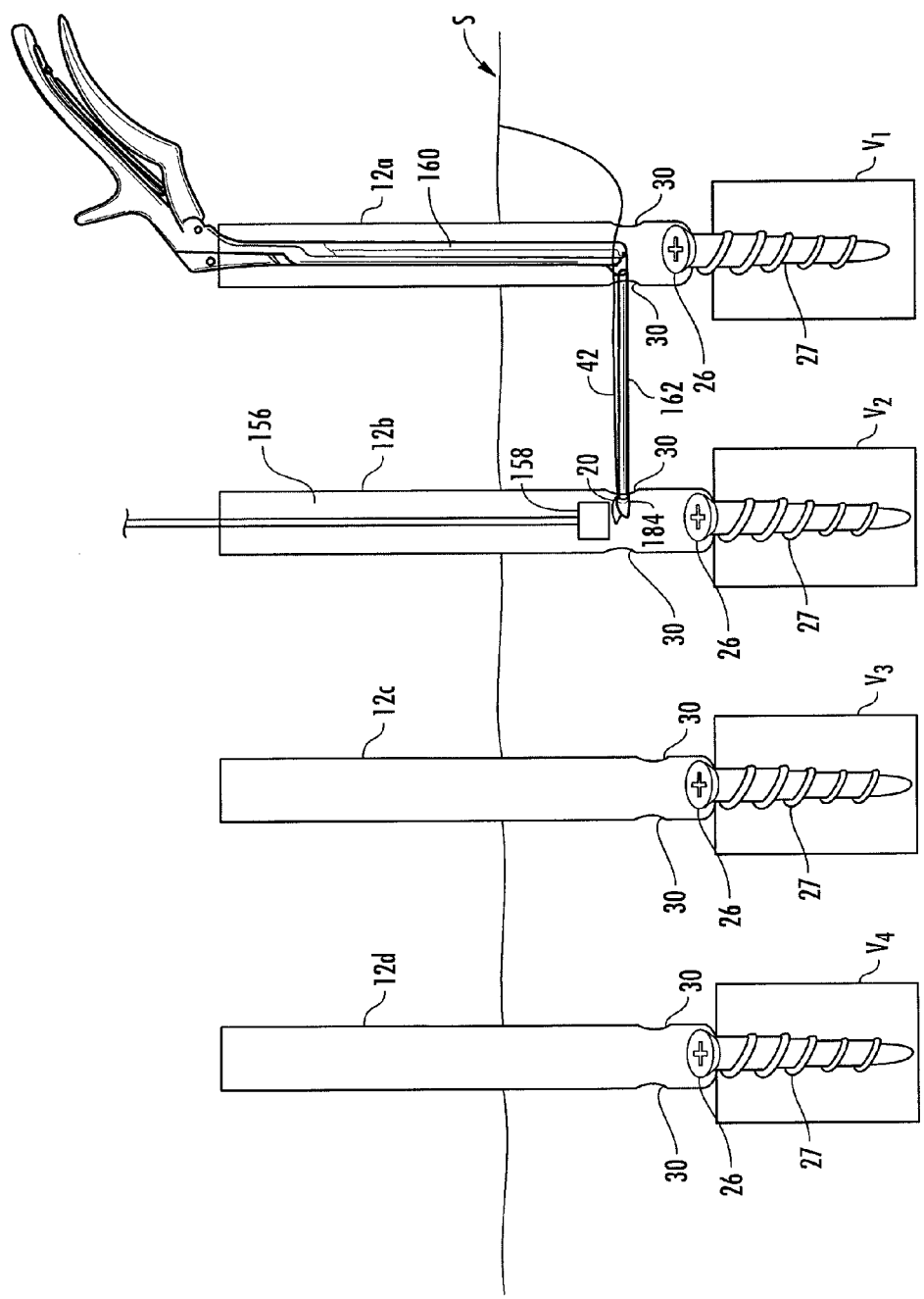
Figure 11E:
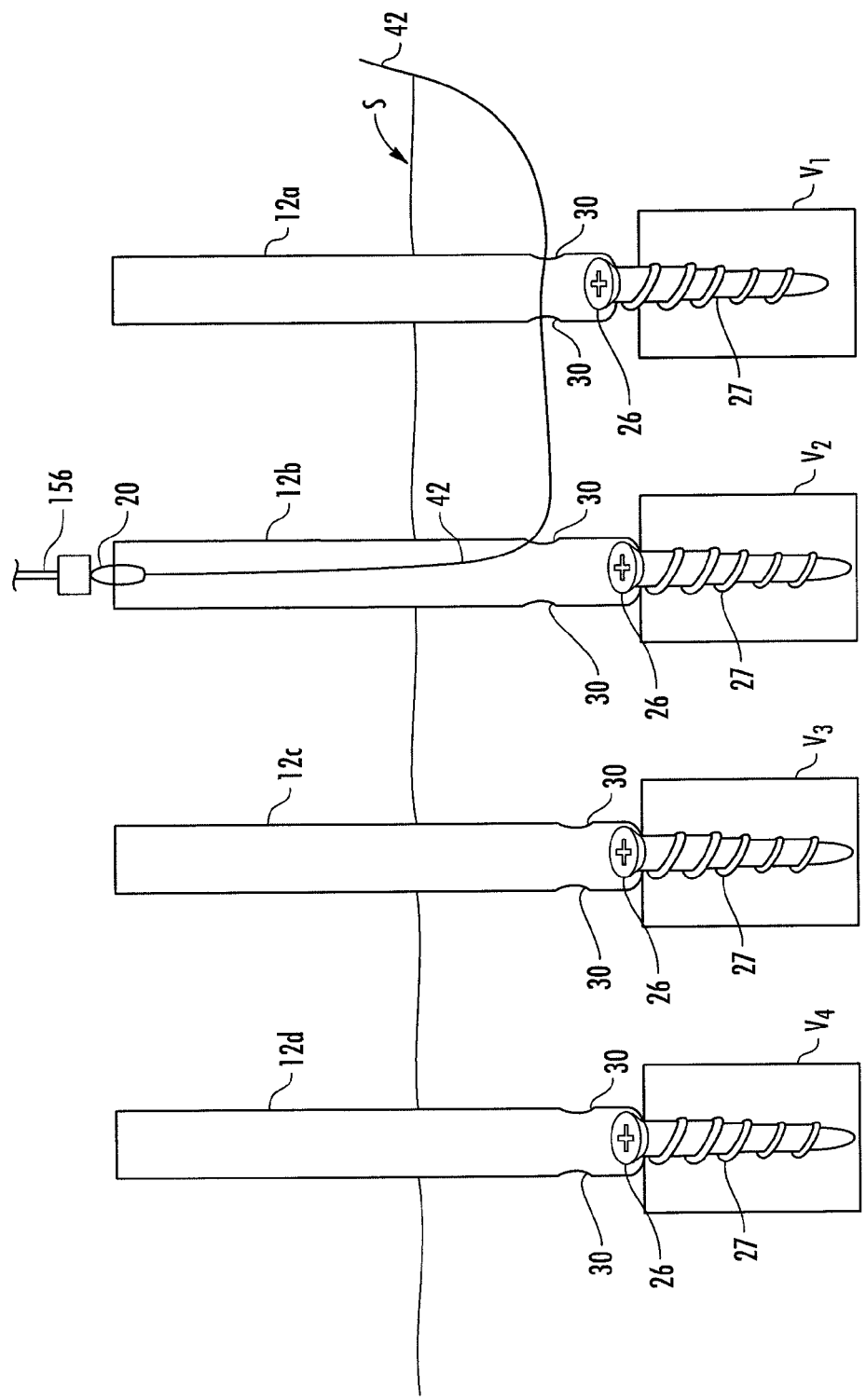
Figure 11F:
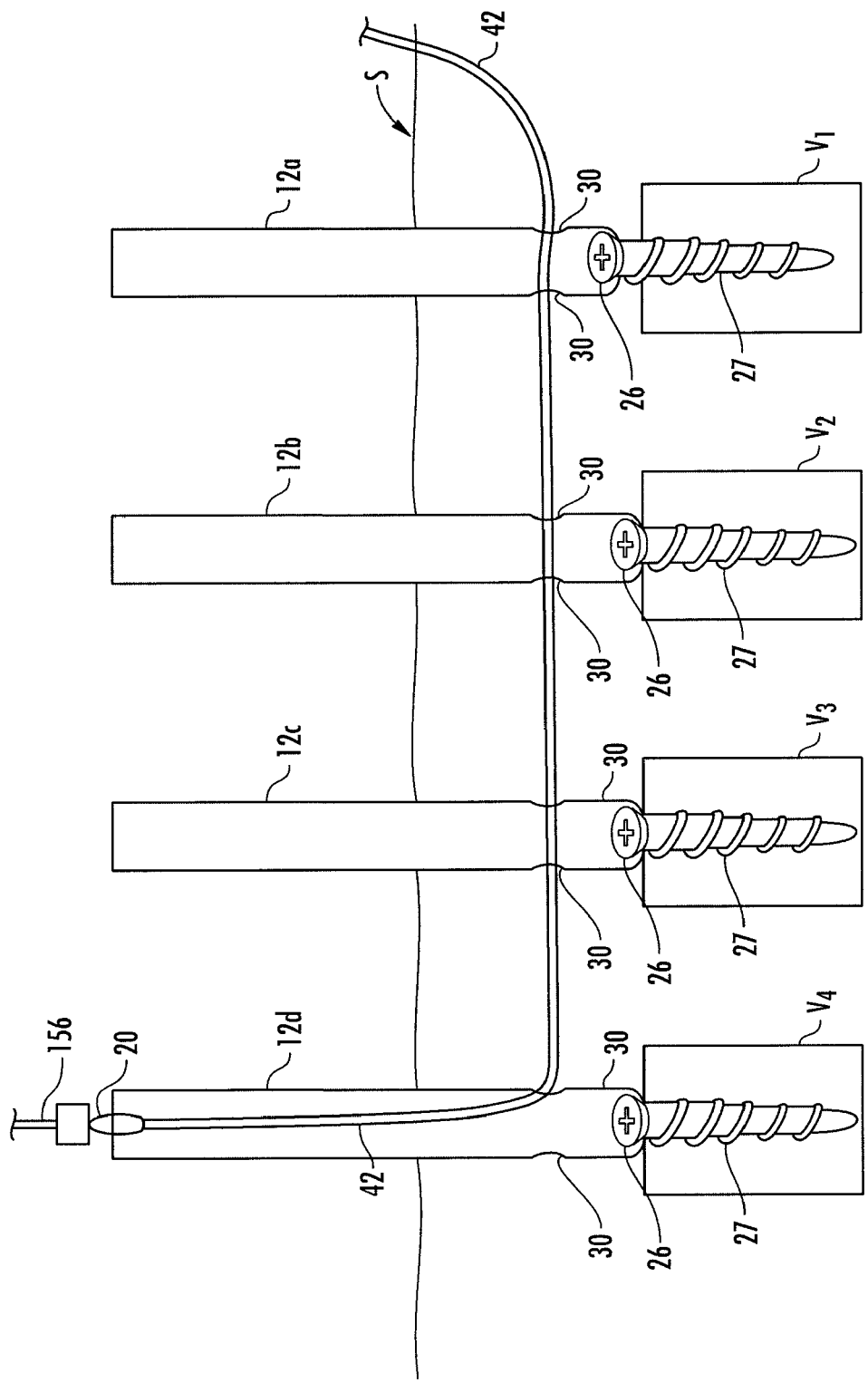

FIGS. 11A through 11F illustrate various steps necessary to position the targeting member such that the connected biocompatible device is positionable relative to multiple target areas. As shown in FIG. 11A an incision I is made to the right of extender 12a. Extender 12a is attached to vertebral body V1. Targeting member 20 is placed in cavity 184 formed on the distal end of passer member 162. A tether 42 is attached to targeting member 20. As the wand 160 is moved downward within the incision I the trigger mechanism is actuated and the passer element 162 is pivoted into a position that is proximate to the lower end of the extender 12a. In this position the targeting member 20 is within the reach of the removal tool 156. While shown with tool 156, it should be understood that tool 150 previously discussed is also suitable. FIG. 11B shows the targeting member 20 exiting the upper portion of the extender 12a. FIG. 11C shows the wand 160 moving down the extender 12a after the targeting member 20 has been positioned within the cavity 184 on passer element 162. FIG. 11D illustrates the targeting member being passed from the first target area to the second target area. As the wand 160 descends extender 12a, the wand is actuated thereby causing a pivotal movement to passer element 162. As the wand 160 proceeds to the bottom of the extender, the distal end of passer element 162 is proximate to the lower interior portion of extender 12b. At this point the targeting member 20 is within reach of removal tool 156. FIG. 11E shows the targeting member 20 and magnetic removal tool 156 exiting the upper portion of the extender 12b. This process is then replicated with respect to passing the targeting member 20 and tether 42 between extenders 12b and 12c, as well as between extenders 12c and 12d. FIG. 11F shows the targeting member 20 and magnetic removal tool 156 exiting the upper portion of extender 12d. Once the targeting member is withdrawn, the surgeon can grasp the targeting member and the attached tether 42. The tether 42 is then used by the surgeon to gently pull the attached biocompatible member (such as a rod) along the path formed through the tissue by the targeting member and through the connector portion of the pedicles until the rod is interconnected with each of the vertebral bodies. As an alternative to starting the process with an incision alongside the first extender 12a, the initial targeting member 20 insertion could be through the upper portion of extender 12a. Likewise, this same process could be used in an environment without extender tubes such as that shown and described in FIG. 8. This technique is particularly useful in navigating a member through more than three vertebral bodies, making it especially beneficial for patients with scoliosis.

Although the invention is described with reference to stabilization and fusion of adjacent spinal vertebrae, it is hereby contemplated that devices and methods disclosed herein could be used in all types of joints (ankle, interdigital, etc.) found in the human or animal body. Although a rod-like member is exemplified herein, other such biocompatible devices known to one skilled in the art are also contemplated, for example, plates, clamps, etc.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical tool suitable for facilitating guiding a biocompatible device to a target area located in vivo, said tool comprising: a tether; and a wand assembly, said wand assembly including a hand grip portion, a central portion and a passer member portion, said hand grip portion constructed and arranged to be grasped by a human hand, said central portion providing spacing between said hand grip portion and said passer member portion, said passer member portion pivotably connected to said central portion for controlled movement about a pivot axis, said passer member portion constructed and arranged for releasable attachment to a first end of said tether, said tether including a second end securable to a biocompatible implant, said hand grip portion including an actuator member operable to cause rotation of said passer member portion about said pivot axis, whereby operation of said actuator member during forward movement of said central portion provides directional progression of said passer member portion and tether member through tissue to said in vivo target area, wherein said passer member portion includes a cavity therein, said cavity sized and configured to cooperate with an enlarged portion of said tether, wherein said enlarged portion of said tether is a targeting member secured to said first end of said tether, wherein said targeting member is secured within said cavity, said targeting member having a first end constructed and arranged to penetrate and create a pathway through tissue as said targeting member is advanced in vivo, wherein said targeting member is constructed of a steering material capable of being magnetically influenced.

2. The surgical tool of claim 1 wherein said actuator member is a trigger member.

3. The surgical tool of claim 1 wherein said central portion of said wand assembly includes a first elongated rod like member fixedly secured to said hand grip portion at a first end and pivotably secured to said passer member portion at a second end, a second elongated rod like member pivotably secured to said actuator member at a first end thereof and pivotably secured to said passer member portion at a second end thereof, whereby movement of said actuator member causes axial displacement of said second rod like member with respect to said first rod like member resulting in the pivotal movement of said passer member portion.

4. The surgical tool of claim 3 including springs positioned to bias said hand grip portion away from said hand grip portion in the absence of external force to said actuator member.

5. The surgical tool of claim 4 wherein said passer member portion axially aligns with said first rod like member in said absence of external force.

6. The surgical tool of claim 1 wherein said passer member portion provides about ninety degrees of controlled rotation about said pivot axis.

7. The surgical tool of claim 6 wherein said rotation of said passer member portion is proportional to movement of said actuator member.

8. The surgical tool of claim 1 wherein said surgical tool is constructed and arranged for use in percutaneous surgical procedures, whereby said surgical tool is inserted directly into a small skin incision.

9. The surgical tool of claim 1 wherein said tool is sized to fit through the central bore of a pedicle screw extender.

10. The surgical tool of claim 1 wherein said passer member portion includes a magnet secured thereto.

11. The surgical tool of claim 1 wherein said tether is a cable.

12. The surgical tool of claim 1 wherein said tether is a cord.

13. The surgical tool of claim 1 wherein said tether is cannulated.

14. The surgical tool of claim 1 wherein said biocompatible implant is a spinal implant.

15. The surgical tool of claim 1 wherein said biocompatible implant is a surgical tool.

16. The surgical tool of claim 1 wherein said surgical tool is constructed and arranged for grasping a tether positioned in a surgical site and repositioning said tether within said surgical site.

* * * * *